US006667411B2

(12) United States Patent
Schattenmann

(10) Patent No.: US 6,667,411 B2
(45) Date of Patent: Dec. 23, 2003

(54) METHOD FOR MAKING ORGANOOXYSILANES

(75) Inventor: Florian Johannes Schattenmann, Ballston Lake, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 09/792,336

(22) Filed: Feb. 26, 2001

(65) Prior Publication Data

US 2001/0047102 A1 Nov. 29, 2001

Related U.S. Application Data

(60) Provisional application No. 60/194,745, filed on Apr. 5, 2000.

(51) Int. Cl.$^7$ .................................................. C07F 7/04
(52) U.S. Cl. ........................ 556/466; 586/470; 586/482; 586/486
(58) Field of Search ................................ 556/466, 470, 556/482, 486

(56) References Cited

U.S. PATENT DOCUMENTS

| 2,442,053 A | 5/1948 | McGregor et al. |
| 2,473,260 A | 6/1949 | Rochow |
| 4,683,321 A | 7/1987 | Nelson |

FOREIGN PATENT DOCUMENTS

| BE | 66451 | 9/1950 |
| DE | 974764 | 4/1961 |
| DE | 3821483 | 6/1988 |
| EP | 430272 A2 | 11/1990 |
| GB | 573906 | 4/1943 |
| LU | 28740 | 12/1947 |

OTHER PUBLICATIONS

Bazant et al., "Organosilicon Compounds", vol. 2, Part 1, p. 109, Academic Press, N.Y., 1965.*
"A Silicate Substitution Route to Organosilicon Compounds", G.B. Goodwin, M.E. Kenney—American Chemical Society, pp. 251–263 (1990).
Abstract—Preparation of Diorganodialkoxysilanes, J. Graefe et al., Jan. 1998, p. 1.
"Reactivity of Lanthanide and Yttrium Hydrides and Hydrocarbyls Toward Organosilicon Hydrides and Related Compounds", A.Z. Voskoboynikov et al., Organometallics 1997, 4041–4055.
"Polymeric Methyl Silicon Oxides", E.G. Rochow et al. pp. 798–780, (1940).
"The Direct Synthesis of Organosilicon Compounds",E.G. Rochow, pp. 963–965 (1945).

* cited by examiner

Primary Examiner—Samuel Barts
(74) Attorney, Agent, or Firm—Bernadette M. Bennett; Patrick K. Patnode

(57) ABSTRACT

A method for the preparation of organooxysilanes containing at least one silicon-carbon bond is provided which comprises reacting at least one tetraorganooxysilane with at least one transition metal organo compound.

12 Claims, No Drawings

METHOD FOR MAKING ORGANOOXYSILANES

This application claims the benefit of provisional application No. 60/194,745 filed Apr. 5, 2000.

STATEMENT REGARDING FEDERALLY SPONSORED RESEARCH & DEVELOPMENT

The government may have certain rights in this invention pursuant to contract number DE-FC02-98CH10931 awarded by the United States Department of Energy.

BACKGROUND OF THE INVENTION

The present invention relates to a method for making organooxysilanes. More particularly, the present invention relates to a process involving the reaction of a tetraorganooxysilane in the presence of a transition metal organo compound.

Organooxysilanes are silicon-containing compounds of the formula $R_mSi(RO)_n$ where each R independently represents a monovalent hydrocarbon group such as an alkyl group, aryl group, aralkyl group, alkaryl group, cycloalkyl group, or bicycloalkyl group; "n" is in a range between 1 and 3; "m" is in a range between 1 and 3; and "n+m" is 4. Silicon-containing compounds with silicon-carbon bonds, such as organooxysilanes, are commonly made from silicon dioxide via elemental silicon. Unfortunately, elemental silicon is manufactured from silicon dioxide by an energy intrusive reduction process.

The process commonly used for the production of silicones was first described by Rochow et al., U.S. Pat. No. 2,473,260. The Rochow process uses silicon, also referred to as elemental silicon, as a starting material. Other possible, alternative precursors for the production of silicones are organooxysilanes. However, the current production of organooxysilanes uses elemental silicon as the starting material and a multi-step reaction is necessary to convert the elemental silicone to an organooxysilane. To prepare elemental silicon, silicon dioxide must be reduced. It is well known in the art that the silicon-oxygen bond in silicon dioxide is extremely stable. In order to break the silicon-oxygen bond, a large amount of energy is consumed when silicon dioxide is reduced to elemental silicon. Thus, due to the large amount of energy needed to break the silicon-oxygen bond, the synthesis of silicones from silicon dioxide using the Rochow process as well as organooxysilanes is expensive and not energy efficient.

In the past, the synthesis of silicon-containing compounds with silicon-carbon bonds has relied heavily on the reduction of silicon dioxide to elemental silicon. Thus, new synthetic routes are constantly being sought which can form silicon-carbon bonds.

BRIEF SUMMARY OF THE INVENTION

The present invention provides a method for the preparation of organooxysilanes containing at least one silicon-carbon bond comprising reacting at least one tetraorganooxysilane with at least one transition metal organo compound.

DETAILED DESCRIPTION OF THE INVENTION

The present invention relates to a process involving the reaction of a tetraorganooxysilane and a transition metal organo compound to form an organooxysilane containing at least one Si—C bond. Tetraorganooxysilanes are of the formula $(RO)_4Si$ where each R independently represents a monovalent hydrocarbon group such as alkyl radicals, aryl radicals, aralkyl radicals, alkaryl radicals, cycloalkyl radicals, or bicycloalkyl radicals. The term "alkyl radical" is intended to designate both normal alkyl and branched alkyl radicals. Normal and branched alkyl radicals are preferably those containing carbon atoms in a range between about 1 and about 22, and include as illustrative non-limiting examples methyl, ethyl, propyl, isopropyl, butyl, tertiary-butyl, pentyl, neopentyl, hexyl, octyl, decyl, dodecyl. Aryl radicals include an example such as phenyl. Cyclo- or bicycloalkyl radicals represented are preferably those containing ring carbon atoms in a range between about 3 and about 12 with a total number of ring carbon atoms less than or equal to about 50. Some illustrative non-limiting examples of cycloalkyl radicals include cyclobutyl, cyclopentyl, cyclohexyl, methylcyclohexyl, and cycloheptyl. Preferred aralkyl radicals are those containing carbon atoms in a range between about 7 and about 14; these include, but are not limited to, benzyl, phenylbutyl, phenylpropyl, and phenylethyl. Typical tetraorganooxysilanes include tetraalkoxysilanes such as tetramethoxysilane, tetraethoxysilane, and tetraiso-propoxysilane; mixed tetraalkoxysilanes such as dimethoxydiethoxysilane; tetraaryloxysilanes such as tetraphenoxysilane; as well as mixed tetra(alkoxyaryloxy)silanes such as dimethoxydiphenoxysilane.

Typical transition metal organo compounds include those wherein the organo group includes alkyl radicals, aryl radicals, aralkyl radicals, alkaryl radicals, cycloalkyl radicals, or bicycloalkyl radicals which are defined above. The transition metal organo compounds include, but are not limited to, bis(cyclopentadienyl)-dimethylzirconium, bis(cyclopentadienyl)dimethyltitanium, bis(cyclopentadienyl)-dimethylvanadium, (pentamethylcyclopentadienyl)-tetramethyltantalum, hexamethyltungsten, methylrheniumtrioxide, tetramethylrheniumoxide, carbonyl(chloro)(iodo)-methylbis(triphenylphosphine)rhodium, carbonyl(chloro)(iodo)methylbis-(triphenylphosphine)iridium, bis(cyclopentadienyl)-diphenylzirconium, and bis(cyclopentadienyl)dimethylzirconium.

Organooxysilanes are compounds of the formula $R_mSi(RO)_n$ where R is defined as above, "n" is in a range between 1 and 3, "m" is in a range between 1 and 3, and "n+m" is 4. Typically, R is methyl, n is 3 and m is 1.

The synthesis typically is typically carried out under an inert gas atmosphere, for example, under a blanket of argon gas, nitrogen gas, or helium gas. The transition metal organo compound is dissolved in an anhydrous solvent such as, for example, methylene chloride or toluene. The reaction between the tetraorganooxysilane and the transition metal organo compound may be carried out at a temperature at or greater than room temperature. More typically, the temperature is in a range between about 50° C. and about 120° C.

The reaction of the present invention can be performed in batch, continuous, or semi-continuous mode. With a batch mode reaction, for instance, all of the components are combined and reacted until most of the reactants are consumed. In order to proceed, the reaction has to be stopped and additional reactant added. A fixed bed and stirred bed may both be run under batch conditions. In contrast, a fluidized reactor is typically run under continuous conditions. With continuous conditions, the reaction does not have to be stopped in order to add more reactants. With semi-continuous conditions, the reaction is typically stopped to add more reactants.

The tetraorganooxysilane is typically added in a mole ratio of transition metal organo compound to tetraorganooxysilane in a range between about 0.15 and about 4 and commonly, a mole ratio of transition metal organo compound to tetraorganooxysilane in a range between about 0.25 and 2.

Products in the organooxysilane synthesis may be isolated by any convenient means. Typically, product(s) may be isolated by filtration, crystallization or distillation. Products may be further purified by any convenient means such as distillation. The formation of the organooxysilane may be confirmed by such methods as gas chromatography (GC), gas chromatography-mass spectroscopy (GC/MS), and proton nuclear magnetic resonance spectroscopy ($^1$H-NMR), carbon nuclear magnetic resonance spectroscopy ($^{13}$C-NMR) and silicon nuclear magnetic resonance spectroscopy ($^{29}$Si-NMR).

An important advantage of using a tetraorganooxysilane and transition metal organo compounds as starting materials for the preparation of organooxysilanes with at least one silicon-carbon bond is that it is energy efficient. The present invention does not require the reduction of silicon dioxide to elemental silicon.

Organooxysilanes obtained by the present method may be used in a wide variety of applications. For example, organooxysilanes may be used as precursors to silicones and organofunctional silicon compounds, precursors to pure and ultra-pure silicon dioxide, coupling agents, additives for plastic applications, and adhesion promoters.

In order that those skilled in the art will be better able to practice the invention, the following examples are given by way of illustration and not by way of limitation.

EXAMPLE 1

All manipulations were performed on a high-vacuum line under argon atmosphere. Bis(cyclopentadienyl)-dimethylzirconium (0.92 grams; 3.7 millimoles) was charged into a 50 milliliter Schlenk flask and dissolved in anhydrous toluene (3 mL). Tetramethoxysilane (0.55 milliliters; 0.56 grams; 3.7 millimole) was added to the stirring solution at room temperature. After 2 hours of stirring at room temperature, the solution was stirred under reflux for 2 hours. After cool down to room temperature, an aliquot of the solution was filtered through silica gel and analyzed by gas chromatography and gas chromatography/mass spectroscopy.

The mixture contained 2% of MeSi(OMe)$_3$ (based on Si(OMe)$_4$) and traces of Me$_2$Si(OMe)$_2$.

EXAMPLE 2

Similar to Example 1, the tetramethoxysilane (0.62 mL; 0.64 g; 4.18 mmol) was added to a solution of bis(cyclopentadienyl)dimethylzirconium (1.05 g; 4.18 mmol) in anhydrous toluene (3 mL) at room temperature. The mixture was heated for 28 h under reflux. The mixture contained 12% of MeSi(OMe)$_3$ (based on Si(OMe)$_4$) and 1.3% of Me$_2$Si(OMe)$_2$.

While typical embodiments have been set forth for the purpose of illustration, the foregoing description should not be deemed to be a limitation on the scope of the invention. Accordingly, various modifications, adaptations, and alternatives may occur to one skilled in the art without departing from the spirit and scope of the present invention.

What is claimed is:

1. A method for the preparation of organooxysilanes containing at least one silicon-carbon bond comprising reacting at least one tetraorganooxysilane with at least one transition metal organo compound.

2. The method according to claim 1, wherein the tetraorganooxysilane comprises tetraalkoxysilanes, tetraaryloxysilanes, tetra(alkoxyaryloxy)silanes, or combinations thereof.

3. The method according to claim 2, wherein the tetraorganooxysilane comprises tetramethoxysilane.

4. The method according to claim 1, wherein the transition metal organo compound is selected from the group consisting essentially of bis(cyclopentadienyl)-dimethylzirconium, bis(cyclopentadienyl)dimethyltitanium, bis(cyclopentadienyl)-dimethylvanadium, (pentamethylcyclopentadienyl)tetramethyltantalum, hexamethyltungsten, methylrheniumtrioxide, tetramethylrheniumoxide, carbonyl(chloro)(iodo)-methylbis(triphenylphosphine)rhodium, carbonyl(chloro)(iodo)methylbis-(triphenylphosphine)iridium, bis(cyclopentadienyl)-diphenylzirconium, and bis(cyclopentadienyl)dimethylzirconium.

5. The method according to claim 4, wherein the transition metal organo compound comprises bis(cyclopentadienyl) dimethylzirconium.

6. The method according to claim 5, wherein the reaction is operated in batch mode.

7. The method according to claim 5, wherein the reaction is operated in continuous mode.

8. The method according to claim 1, wherein the reaction is conducted at a temperature at or greater than about room temperature.

9. The method according to claim 8, wherein the reaction is conducted at a temperature in a range between about 50° C. and about 120° C.

10. The method according to claim 1, wherein the transition metal organo compound is present in a mole ratio of transition metal organo compound to tetraorganooxysilane in a range between about 0.15 and about 4.

11. The method according to claim 10, wherein the transition metal organo compound is present in a mole ratio of transition metal organo compound to tetraorganooxysilane in a range between about 0.25 and about 2.

12. A method for the preparation of methyltrimethoxysilane comprising reacting tetramethoxysilane with bis(cyclopentadienyl)dimethylzirconium wherein the bis(cyclopentadienyl)dimethylzirconium is present in a mole ratio of bis(cyclopentadienyl)dimethylzirconium to tetramethoxysilane in a range between about 0.5 and about 1.2.

* * * * *